(12) United States Patent
Shaw et al.

(10) Patent No.: US 9,186,169 B2
(45) Date of Patent: Nov. 17, 2015

(54) SNARE WITH LOOP MADE OF HEAT SHRINKABLE SHAPE MEMORY MATERIAL AND METHOD OF USE THEREOF

(75) Inventors: William J. Shaw, Cambridge, MA (US); Kristian Dimatteo, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 990 days.

(21) Appl. No.: 12/766,054

(22) Filed: Apr. 23, 2010

(65) Prior Publication Data

US 2010/0204710 A1      Aug. 12, 2010

Related U.S. Application Data

(63) Continuation of application No. 11/250,921, filed on Oct. 14, 2005, now abandoned.

(51) Int. Cl.
*A61B 17/24* (2006.01)
*A61B 17/3205* (2006.01)
*A61B 17/00* (2006.01)

(52) U.S. Cl.
CPC . *A61B 17/32056* (2013.01); *A61B 2017/00867* (2013.01)

(58) Field of Classification Search
CPC ................ A61B 17/32056; A61B 2017/00867
USPC .................................................. 606/113, 114
See application file for complete search history.

(56) References Cited

U.S. PATENT DOCUMENTS

| | | |
|---|---|---|
| 3,476,115 A | 11/1969 | Claude et al. |
| 4,018,229 A | 4/1977 | Komiya |
| 4,425,908 A | 1/1984 | Simon |
| 4,493,320 A | 1/1985 | Treat |
| 5,201,741 A | 4/1993 | Dulebohn |
| 5,330,483 A | 7/1994 | Heaven et al. |
| 5,352,184 A | 10/1994 | Goldberg et al. |

(Continued)

FOREIGN PATENT DOCUMENTS

WO        WO 02/39913        5/2002

OTHER PUBLICATIONS

International Search Report and Written Opinion for PCT Application No. PCT/US2006/037200, dated Jan. 17, 2007 (11 pages).

*Primary Examiner* — Kathleen Holwerda
*Assistant Examiner* — Sarah Simpson
(74) *Attorney, Agent, or Firm* — Bookoff McAndrews, PLLC

(57) ABSTRACT

A tissue snare comprises an elongated member having a distal end and a loop formed of a shape memory material, the loop including a tissue receiving interior opening and being connected to the distal end of the elongated member, properties of the shape memory material being selected so that, when a temperature of the loop exceeds a critical temperature thereof, the loop constricts from an expanded state to a constricted state. A method of treating tissue comprises placing a loop of a snare around a portion of tissue to be treated while the loop is in an expanded configuration, the loop being formed of a shape memory material having a critical temperature so that, when a temperature of the loop is above the critical temperature, the loop transitions from the expanded configuration to a constricted configuration in combination with transitioning, after the loop has been placed around the portion of tissue to be treated, the loop from the expanded configuration to the constricted configuration to tighten the loop around the portion of tissue to be treated.

16 Claims, 2 Drawing Sheets

(56) References Cited

U.S. PATENT DOCUMENTS

| | | |
|---|---|---|
| 5,611,803 A | 3/1997 | Heaven et al. |
| 5,716,410 A | 2/1998 | Wang et al. |
| 5,746,747 A | 5/1998 | McKeating |
| 6,015,415 A | 1/2000 | Avellanet |
| 6,240,630 B1 | 6/2001 | Lee et al. |
| 6,388,043 B1 | 5/2002 | Langer et al. |
| 6,773,432 B1 * | 8/2004 | Clayman et al. ............ 606/41 |
| 6,786,884 B1 | 9/2004 | DeCant, Jr. et al. |
| 7,135,018 B2 | 11/2006 | Ryan et al. |
| 7,151,157 B2 | 12/2006 | Mather |
| 2002/0165555 A1 * | 11/2002 | Stein et al. ............ 606/113 |
| 2003/0236531 A1 | 12/2003 | Couvillon, Jr. |
| 2005/0043743 A1 * | 2/2005 | Dennis ............ 606/113 |
| 2005/0049613 A1 | 3/2005 | Brown |
| 2006/0009785 A1 * | 1/2006 | Maitland et al. ............ 606/113 |

\* cited by examiner

SNARE WITH LOOP MADE OF HEAT SHRINKABLE SHAPE MEMORY MATERIAL AND METHOD OF USE THEREOF

PRIORITY CLAIM

The present application is a Continuation of U.S. patent application Ser. No. 11/250,921 filed on Oct. 14, 2005, the entire disclosure of the above-identified application expressly incorporated herein by reference.

BACKGROUND

Polyps are abnormal growths that typically extend from an inner wall of a hollow organ and may be precursors to more serious ailments such as cancer. Polyps may develop in different parts of a patient's body, for example the gastro intestinal (GI) tract, the uterus, the heart, etc. However, polyps which develop in the intestine, especially in the colon and the rectum, are serious as they are often a precursor for colorectal cancer. Thus, treatment of these polyps before they develop into malignancies is extremely important.

Several procedures available for the removal of polyps generally are applicable to colorectal polyps in particular. Snares are commonly used to grip and remove polyps. In some instances, the polyp is not immediately removed. Rather, the snare is tightened around the polyp and left in place to act as a ligation band, choking the supply of blood to the polyp so that it withers and dies over time.

Various types of snares are commonly used to remove polyps, for example from the intestine wall. These snares all require a mechanism to tighten a loop of the snare around the polyp so that it can be gripped and removed from the underlying tissue layers. Generally, the tightening is done mechanically, by providing a linkage between the loop and a control handle, so that the surgeon can manually tighten the loop. Levers, pulleys, cables or other devices may be used to facilitate the tightening of the loop around the polyp. However, the linkages connecting these loops to the controls and associated elements is often bulky, making the snare device too large to be inserted endoscopically and/or to be manipulated as necessary.

Polyps may also be removed through hot biopsy in which a forceps is used to grip the polyp between jaws which are heated to ablate the base of the polyp so it can be retrieved and evaluated. Destructive techniques such as argon beam coagulation are also used to treat polyps. In these procedures, energy (e.g., laser energy) is directed to the polyp to necrose the tissue.

SUMMARY OF THE INVENTION

In one embodiment, the present invention is directed to a tissue snare comprising an elongated member having a distal end and a loop formed of a shape memory material, the loop including a tissue receiving interior opening and being connected to the distal end of the elongated member, properties of the shape memory material being selected so that, when a temperature of the loop exceeds a critical temperature thereof, the loop constricts from an expanded state to a constricted state.

The present invention is further directed to a method of treating tissue comprising placing a loop of a snare around a portion of tissue to be treated while the loop is in an expanded configuration, the loop being formed of a shape memory material having a critical temperature so that, when a temperature of the loop is above the critical temperature, the loop transitions from the expanded configuration to a constricted configuration in combination with transitioning, after the loop has been placed around the portion of tissue to be treated, the loop from the expanded configuration to the constricted configuration to tighten the loop around the portion of tissue to be treated.

DETAILED DESCRIPTION

Figure 1:
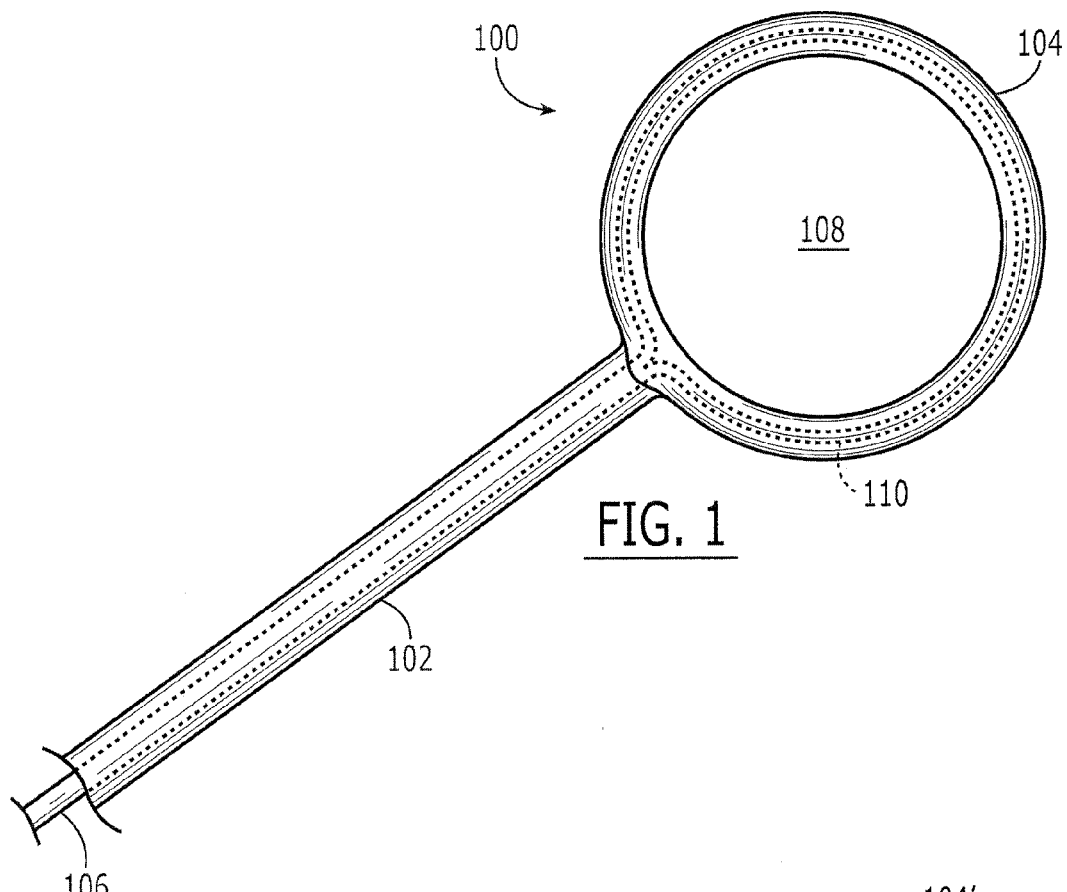
FIG. 1 is a diagram showing a snare device to remove polyps according to the present invention, in an open configuration.

The present invention may be further understood with reference to the following description and the appended drawings, wherein like elements are referred to with the same reference numerals. The present invention relates to devices for removing polyps from hollow organs and, in particular, relates to a snare for removing intestinal polyps. The present invention relates generally to the treatment of diseases and injuries to tissue that respond to constriction of the tissue and may be used, for example, to treat bleeding by forming a constriction around an injured portion of tissue.

Conventional treatments for polyps, particularly intestinal polyps, include hot biopsy, snaring and ablation. During ablation, energy is supplied to the polyp to disrupt cellular activity. For example, laser energy may be directed to the polyp in the form of an argon beam or other laser beam, to cause coagulation and necrosis. RF or other electrical energy may be used to heat a device, a target portion of tissue or both.

Ablation and other destructive techniques are often used when colonoscopy or other endoscopic procedures for removing and collecting the polyp cannot be performed (e.g., for reasons related to the patient's health). Because these procedures destroy the tissue, they do not allow for a biopsy of the polyp to determine, for example, whether the polyp is cancerous. Thus, these treatments are not as favored as those which remove the tissue intact.

One common method of achieving this result is a hot biopsy procedure. In this procedure, a distal end of a forceps is placed in proximity to the polyp and clamps of the forceps are placed around the base of the polyp. The clamps are then heated to cauterize and ablate the base of the polyp, detaching the polyp from the surrounding tissue. The balance of the polyp is available substantially undamaged for collection and biopsy. This procedure is often used to treat relatively small polyps, where the clamps of the forceps can be placed around the base of the polyp with the heat serving to aid in hemostasis.

Snaring, which is also commonly used to remove polyps, involves positioning a loop around the base of a polyp and tightening the wire therearound so that the loop closes around the polyp, slicing it from the wall of the underlying organ. This procedure is commonly carried out to remove polyps in the bowels, so that they may be retrieved and biopsied. With conventional snares, the loop is tightened through manual operation of an actuator coupled to the snare by a mechanical linkage, for example, by squeezing a hand control or moving a lever coupled to a control wire which is attached to the snare. Polyps of various sizes may be treated in this manner by employing snares of different dimensions.

However, the actuators and mechanical linkages used to tighten the loop increase the size of these devices which may make them too large for use in certain endoscopic and other minimally invasive procedures. Particularly, snare devices are often inserted into the body through endoscopes or colonoscopes. Additionally, since the devices are actuated manually, it may be difficult to maintain the snare in the proper position over the polyp while, at the same time, tightening the loop around the polyp. This issue is more serious when treating small polyps in difficult to reach places. Conventional snare devices tend to be straight, with a long, relatively inflexible deployment cannula. Thus these devices are unsuitable for polyps in certain, less accessible locations. In addition, such manually operated devices comprise mechanical components which may fail during use. Furthermore, assembly complexity and manufacturing costs are increased with the addition of these components.

A device according to the present invention includes a snare with a loop formed of a shape memory material. As would be understood by those skilled in the art, a variety of known metal alloys and polymers may be manufactured with shape memory properties. Shape memory refers to the ability of the material to "memorize" a shape, so that, after being forced into another shape by strain, i.e. application of a force thereto, they return to the originally memorized shape under predetermined conditions. Generally, the change in condition which brings about a return to the original memorized condition is a change in temperature above or below a critical temperature. For example, a shape memory material may be formed into a wire having a certain length. The wire may then be cooled below its critical temperature and subject to a strain to stretch the wire to a greater length, where it will remain until heated above the critical temperature. When the temperature of the wire exceeds the critical temperature, it will return to its original shorter length.

Those skilled in the art will understand that several metallic alloys have been developed which possess shape memory properties. For example, Nitinol which is an alloy containing nickel and titanium possesses shape memory properties that are well suited for application in medical implants. These alloys exist in one of two different temperature-dependent crystal structures which correspond to an austenitic phase and a martensitic phase. At temperatures below a critical temperature, these alloys are martensitic. The martensite phase of these alloys is soft and ductile and can be easily deformed by de-twinning the crystalline structure via an applied strain. At temperatures above the critical temperature, the alloys are austenitic. Austenite is a strong and hard phase of these alloys, exhibiting properties similar to those of titanium, and is characterized by a much more regular crystalline lattice structure. These alloys may also undergo a phase change as a result of the application of strain. For example, an element in the austenitic phase may be bent so that, at high strain locations, the alloy becomes martensitic. If the alloy is designed to have an unstable martensite phase at a selected operating temperature, removal of the strain results in a reverse transformation that straightens the bending. The strain may be removed, for example, by heating the alloy above the critical temperature.

Polymeric shape memory materials have properties similar to those of the metallic shape memory alloys, although those properties result from different physical effects and processes. As such, elements formed from shape memory polymers may be given a base shape and then cooled below the critical temperature where a strain is applied to deform the polymer. When the element is heated again to a temperature above the critical temperature, it regains the shape that it had before the strain was applied. Examples of polymers that have been utilized in hard and soft phases of shape memory polymers include polyurethanes, polynorborenes, polyethers, polyacrylates, polyamides, polysiloxanes, polyether amides, polyether esters, trans-polyisoprenes, polymethylmethacylates, cross-linked trans-polyoctylenes, cross-linked polyethylenes, cross-linked polyisoprenes, cross-linked polycyclooctenes, inorganic-organic hybrid polymers, co-polymer blends with polyethylene and Kraton, styrene-butadiene co-polymers, urethane-butadiene co-polymers, PMMA, polycaprolactone or oligo caprolactone co-polymers, PLLA or PL/D LA co-polymers, PLLA PGA co-polymers, and photo-crosslinkable polymers including azo-dyes, zwitterionic, and other photochromatic materials such as those described in "Shape Memory Materials" by Otsuka and Wayman, Cambridge University Press 1998, the entire contents of which are incorporated herein by reference.

For example, a wire formed of a shape memory material may contract when warmed above the critical temperature causing the wire to shrink and, if formed as a snare, contraction of the loop of the wire will cause the snare to constrict. In an exemplary use of the device according to the invention, a loop of a snare is inserted into the intestine in an expanded configuration via, for example, a colonoscope or other endoscopic instrument. The material of which the snare is formed is preferably designed so that a critical temperature of the material is a selected amount above an ambient temperature in the environment in which the snare is to be deployed (e.g., body temperature) so that the timing of contraction of the snare may be controlled by selectively heating the snare to the critical temperature when phase change is desired. Alternatively, a material with a critical temperature lower than body temperature may be selected so that the snare is deployed as it warms above the critical temperature.

The loop is positioned around a polyp while the wire is still in the expanded configuration (i.e., before the wire is warmed to the critical temperature). Then, as the temperature of the loop approaches body temperature or is heated to the critical temperature, the shape memory properties of the wire are activated causing it to shrink and tighten around the base of the polyp. Those skilled in the art will understand that the snare may be designed to tighten until the polyp is cut off from the underlying tissue or until blood flow to the polyp is cut off. When tightened to the point of resection, the polyp will be left intact for retrieval and biopsy while, in the case of the cut off of blood flow, the polyp will slowly whither and slough off.

Pedunculated polyps may be treated directly with the exemplary loop, by placing the loop around the polyp's stalk before heating. Polyps without stalks (e.g., flap and sessile polyps) may require an injection of a fluid under their bases before they are elevated from the underlying tissue sufficiently to be removed by the snare. Once such a polyp has been elevated from the underlying tissue, the procedure is the same as described above.

In an exemplary embodiment according to the invention, the heating is carried out by controlling circulation of a hot fluid in a heat exchange area in contact with the shape memory material. However, other methods of heating the loop may be used as well. For example, the shape memory material may be heated by an electric element placed adjacent to the loop, embedded within the loop, wrapped around the loop or as a component of the loop, such as a resistor extending proximate to the shape memory element. Other sources of heat located near the loop may also be used, such as active heat sources or conductive elements which convey heat to the shape memory element from a more remote source. Alternatively, an external source may heat the loop. For example, magnetic or electric fields may be used to heat the loop by induction to a temperature greater than the critical temperature, while using a source of energy external to the patient, or remote from the shape memory element. For example, a loop may be formed of a polymer with particles responsive to the applied energy embedded therein. Alternatively, the loop may be heated using focused high frequency ultrasound as would be understood by those skilled in the art.

FIG. 1 shows an exemplary embodiment of a loop snare device according to the invention. The snare device 100 comprises an elongated portion 102 and a loop portion 104. The elongated portion 102 is designed to be inserted into a body, for example, through an endoscope to a target site including a tissue growth (e.g., a polyp) to be removed. In one embodiment, elongated portion 102 is sufficiently resilient so that it is able to support the loop portion 104 as the user positions it proximate to the polyp. The elongated portion 102 also retains a certain amount of flexibility to pass through curving passages of a flexible endoscope extending through, for example, a curved body lumen. The overall dimensions of the snare device 100 are preferably compatible with use through the working channel of an endoscope or colonoscope. For example, a snare device 100 of 0.5-3.5 mm diameter may be suitable for use with a colonoscope having a working channel of 2-4 mm diameter.

The loop element 104 is formed of the shape memory material as described above. In the exemplary embodiment, the shape memory material is a polymer which is maintained below its critical temperature during insertion into the body. To achieve this, the critical temperature may be selected to be higher than body temperature as described above. In this condition as shown in FIG. 1, the loop 104 is expanded to the insertion configuration, with a relatively large opening 108 defined thereby. The loop 104 is selected so that the opening 108, in the insertion configuration, is larger than the polyp to be treated allowing the user to maneuver the elongated portion 102 and the loop 104 over the polyp and around the base thereof. The specific shape of the loop 104 may be varied depending on the procedure being carried out. For example, the loop 104 may be circular, oval or any other conventional shape used in the construction of snare devices. The dimensions of the loop 104 may preferably selected to fit the size of the polyp, being treated and, thus, will vary from case to case. In addition, the snare may be shaped to include a sharp inner surface or tissue cutting blade.

Figure 2:
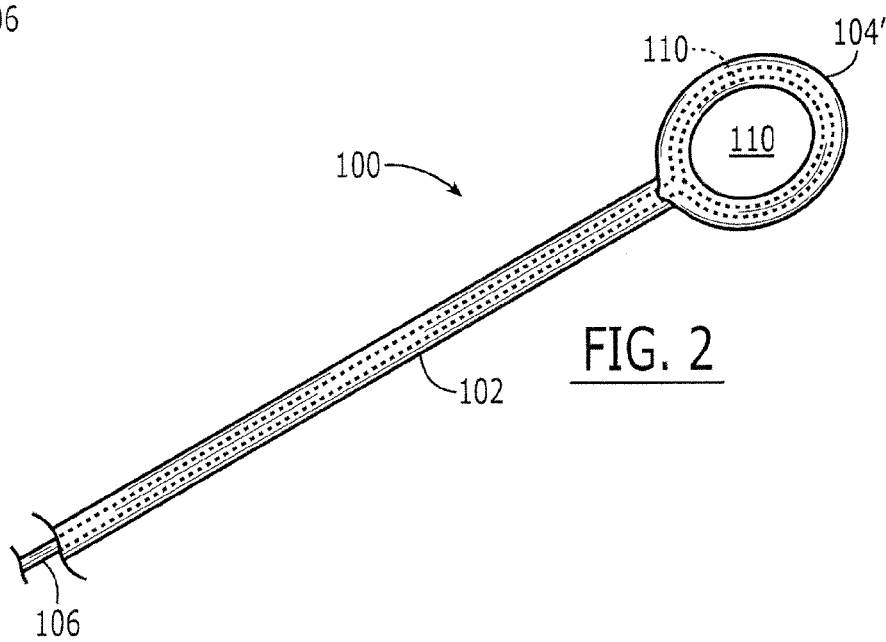
FIG. 2 is a diagram showing the snare device of FIG. 1 in a tightened configuration.

FIG. 2 shows the snare device 100 in the constricted configuration after the loop 104 has been reduced in size to that of the loop 104'. The loop 104 returns to the constricted configuration 104' shown in FIG. 2 after undergoing a reverse transformation. In the case of the exemplary shape memory polymer, the transformation takes place due to heating above a critical temperature. In the embodiment shown in FIGS. 1 and 2, the loop 104, 104' is heated by placing a heated fluid in contact therewith. As shown, a conduit 106 extends through the elongated portion 102, from a proximal source of heated water (not shown) to the loop 104, 104'. Within the loop 104, 104', a second conduit 110 may form a leak-proof path to deliver heated water to the interior of the loop 104, 104' thereby preventing hot fluid from injuring surrounding tissue. In addition, the conduits 106, 110 may provide either a one way or a recirculating flow path. The latter may be carried out by providing a dual lumen conduit 106 and means to move the fluid through loop 104, such as a pump or recirculator as would be understood by those skilled in the art.

Figure 3:
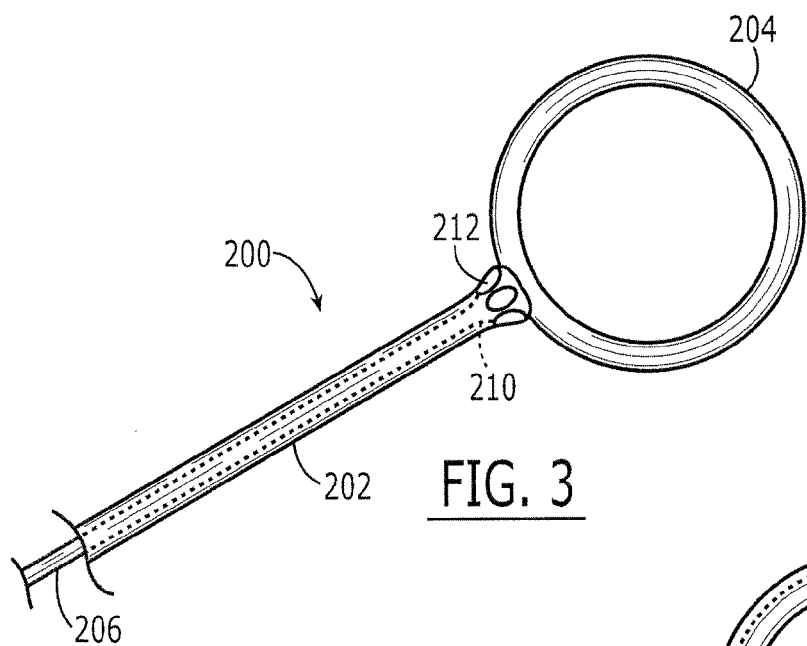
FIG. 3 is a diagram showing another embodiment of the snare device according to the invention.

FIG. 3 shows a different embodiment of a snare device according to the present invention. In this embodiment, the snare device 200 comprises an elongated shaft 202 and a loop portion 204 formed of a shape memory material, for example, a shape memory polymer or alloy which returns to an original, reduced dimension configuration as a result of heating above a critical temperature. A conduit 206, extending along or within the elongated shaft 202 to the loop element 204, conveys heated fluid thereto from a fluid source and terminates in a manifold 210 having a plurality of flow dispensing elements such as nozzles 212, directed towards the loop 204. According to this exemplary embodiment, the heated fluid does not circulate within the loop 204, but rather is provided externally on the shape memory material to cause the contraction of the loop 204.

As compared with loop designs including an internal heated fluid conduit, externalizing the flow of heated fluid around the loop 204 as described above simplifies construction and reduces the cost and difficulty associated with manufacture of the device. However, as the unconstrained heated fluid may damage surrounding tissue, the device may not be suitable for all applications and shielding may be necessary to protect the surrounding tissue from the heated fluid. The heated fluid may include therapeutic compounds to aid in treating the target tissue or, alternatively, may include components which, when mixed generate heat through an exothermic reaction to raise the temperature of the snare over the critical temperature.

Those of skill in the art will understand that additional methods of heating the shape memory elements may be used in the various embodiments of the present invention. As described, a heated fluid may be used, either in a fully contained system as in the embodiment shown in FIGS. 1, 2, or in a system where the fluid is allowed to escape, as in the embodiment of FIG. 3. In addition, the shape memory elements may be heated using different physical principles. For example, electric heating elements may be used to bring about the change in state of the shape memory elements from an expanded configuration to a contracted configuration. Heating of the shape memory material may also be obtained by magnetic or electric induction. For example, a magnetic shape memory material may be heated by generating a magnetic field outside the patient's body, in proximity to the shape memory element.

Figure 4:
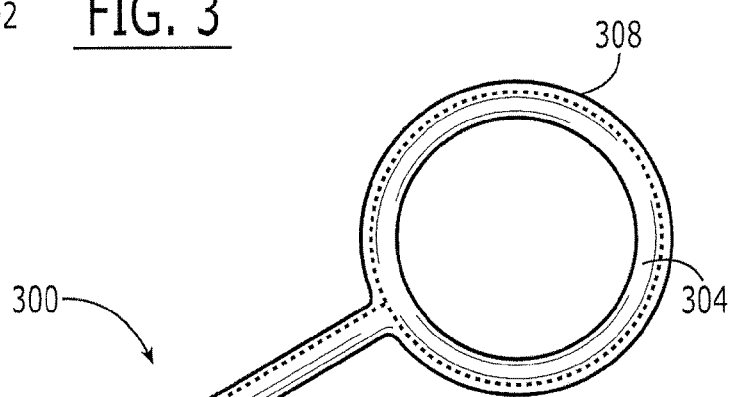
FIG. 4 is a diagram showing a third embodiment of the snare device according to the invention.

FIG. 4 shows a snare device 300 having an elongated shaft 302 connected to a loop portion 304 formed of a shape memory material. An electric connection 306 is provided between a source of electric power (not shown) which, for example, remains outside the body and a heating element 308 in contact with the loop 304. As would be understood by those skilled in the art, the pattern, extent and size of the heating element 308 may be varied to achieve specific amounts and rates of change of various portions of the loop 304 to, for example, control the shape of the loop 304 during and/or after constriction and/or to control the speed of constriction. If the loop 304 is formed of a shape memory metal alloy which conducts electricity, a separate heating element may be unnecessary as the loop 304 may receive current from the power source and serve as the heating element 308.

As described above, the amount of constriction of the loop element according to the present invention depends upon a composition of the shape memory material and an amount of heating provided, among other factors. As described above, a loop snare may be constructed so that the amount of constriction, although insufficient to completely sever the polyp from the underlying tissue, ligates the polyp to cut-off blood supply thereto. Those skilled in the art will understand that an amount of constriction sufficient to sever polyps of a given size, may be obtained by altering the design of the shape memory elements.

Figure 5:
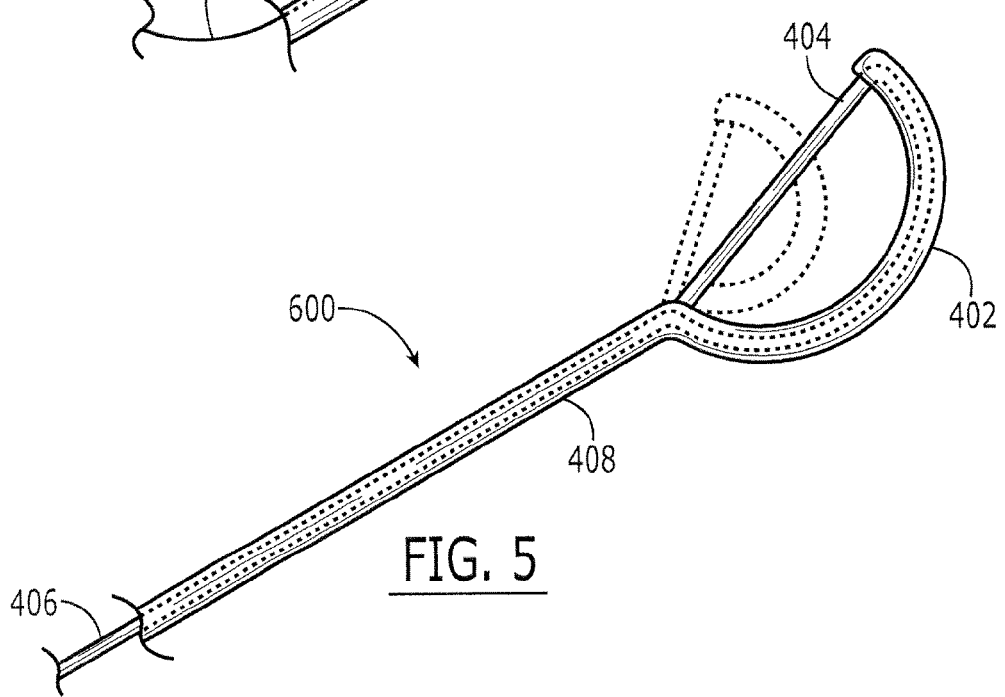
FIG. 5 is a diagram showing a further embodiment of the snare device according to the invention.

For example, FIG. 5 shows a curved shape memory element 402 extending from a shaft 408 of a snare device 400. By selecting an appropriate shape of the shape memory element 402, a mechanical advantage is gained which, when employed with a properly constituted shape memory material allows the snare device 400 to directly remove the targeted polyp from the underlying tissue. Specifically, the device 400 includes a substantially straight cord member 404 which couples a distal end of the curved shape memory element 402 to the distal end of the shaft 408. The cord member 404 is preferably composed of the same shape memory material as the shape memory element 402 so that, when heated, the cord member 408 contracts linearly as the shape memory element 402 constricts around the polyp. Linear contraction of the cord member 404 draws the distal end of the shape memory element 402 toward the distal end of the shaft 408 so that, when combined with the annular constriction of the shape memory element 402, opposed sides of the snare loop are drawn taut adjacent one another along a substantially straight line.

In yet another embodiment according to the present invention, the shape memory material is formed so that its critical temperature is below the average temperature of the human body. In this embodiment, the shape memory material is designed to remain in the stressed configuration at room temperature, and to return to the original configuration as it exceeds the critical temperature while approaching the ambient temperature within the body. For example, the loop of the snare may be made of a shape memory material which retains an open, enlarged configuration when cooled to a temperature lower than its critical temperature which is, in turn, lower than body temperature. When inserted into the body, the loop warms until its temperature exceeds the critical temperature and then constricts to the original, smaller size. As a result, the snare tightens to act as a ligating band or cutting snare as described above.

If it is desired to maintain the shape memory material below the critical temperature so that the shape memory element retains the stressed shape until the snare is properly positioned, for example, around a polyp, a cooling fluid may be supplied to counteract the warming effects of the body heat. For example, a conduit such as that described with reference to FIGS. 1 and 2 may be used to supply cooling fluid instead of a heating fluid. Then, when the snare has reached the desired location and has been placed around a target portion of tissue (e.g., a polyp), the cooling flow is stopped and the body heat raises the temperature of the shape memory element above the critical temperature and constricts the snare. Those skilled in the art will understand that the snare may be made detachable from the applicator so that it may be left in place around the target tissue, functioning like a ligating band.

The present invention has been described with reference to specific exemplary embodiments. Those skilled in the art will understand that changes may be made in details, particularly in matters of shape, size, material and arrangement of parts. Accordingly, various modifications and changes may be made to the embodiments. Additional or fewer components may be used, depending on the condition that is being treated using the snare device. The specifications and drawings are, therefore, to be regarded in an illustrative rather than a restrictive sense.

What is claimed is:

1. A tissue snare, comprising:
an elongated member having a distal end; and
a continuous loop coupled to the elongated member, the loop comprising a shape memory material, the loop including a tissue receiving interior opening and being connected to the distal end of the elongated member, properties of the shape memory material being selected so that, when a temperature of the loop exceeds a critical temperature, at least a first section of the loop extends along a curve and constricts annularly from an expanded state having a first diameter to a constricted state having a second diameter.

2. The snare according to claim 1, wherein the shape memory material is a shape memory polymer.

3. The snare according to claim 1, wherein the shape memory material is a shape memory metal.

4. The snare according to claim 1, further comprising a temperature control apparatus controlling a temperature of the loop to control transitions of the loop between the expanded state and the constricted state.

5. The snare according to claim 4, wherein the temperature control apparatus includes a fluid lumen extending to the distal end of the elongated member to provide one of cooling and heating fluid to the loop.

6. The snare according to claim 5, wherein the temperature control apparatus further comprises a fluid conduit extending along at least a portion of the length of the loop.

7. The snare according to claim 6, wherein the fluid conduit extends from a distal opening of the fluid lumen, within the loop.

8. The snare according to claim 4, wherein the temperature control apparatus further comprises a heating element positioned along at least a portion of the length of the loop.

9. The snare according to claim 8, wherein the heating element is integrally formed with the loop.

10. The snare according to claim 8, wherein the heating element is bonded to an exterior surface of the loop.

11. The snare according to claim 5, further comprising a fluid dispensing opening located adjacent to the distal end of the elongated member for directing fluid from the fluid lumen, toward an exterior surface of the loop.

12. The snare according to claim 5, further comprising a manifold arranged on a distal end of the elongated member, the manifold including at least one opening through which the fluid flows from the fluid lumen to the loop.

13. The snare according to claim 1, wherein the shape memory material is selected so that the critical temperature is greater than an ambient temperature to which the distal end will be exposed when in an operative position.

14. The snare according to claim 1, wherein the first section extends from a distal end of the elongated member to a first section distal end separated from the distal end of the elongated member and wherein the loop includes a second section extending along a substantially straight line between the distal end of the elongated member and the first section distal end.

15. The snare according to claim 14, wherein the second section constricts in a linear manner to bring the distal end of the first section toward the distal end of the elongated member.

16. The snare according to claim 1, wherein end points of the loop are fixed to the distal end of the elongated member.

* * * * *